US00PP21279P2

(12) United States Plant Patent
Utecht

(10) Patent No.: US PP21,279 P2
(45) Date of Patent: Sep. 7, 2010

(54) ***PELARGONIUM* PLANT NAMED 'FISBLIRANGE'**

(50) Latin Name: ***Pelargonium peltatum* (L.) *L'Hérit. ex Ait***
Varietal Denomination: Fisblirange

(75) Inventor: Angelika Utecht, Montabaur (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/456,285

(22) Filed: Jun. 15, 2009

(51) Int. Cl.
*A01H 5/00* (2006.01)

(52) U.S. Cl. ..... Plt./332

(58) Field of Classification Search ..... Plt./332
See application file for complete search history.

*Primary Examiner*—Annette H Para
(74) *Attorney, Agent, or Firm*—S. Matthew Edwards

(57) ABSTRACT

A new *Pelargonium* plant named 'Fisblirange,' particularly distinguished by the brilliant red flower color, open, single-type flowers, early and rich flowering, healthy, medium green foliage with weak to medium expression of zonation, vigorous growth, bushy and well-branched, trailing plant habit.

2 Drawing Sheets

Latin name of the genus and species of the plant claimed: *Pelargonium peltatum* (L.) *L'Hérit. ex Ait.*

Varietal denomination: 'Fisblirange'.

BACKGROUND OF THE NEW PLANT

The present invention comprises a new (ivy) geranium, botanically known as *Pelargonium peltatum* and hereinafter referred to by the variety name 'Fisblirange.'

'Fisblirange' is a product of a planned breeding program. The new cultivar has bright red, single-type flowers, medium green, zoned foliage, vigorous growth, trailing plant habit and very good branching characteristics.

'Fisblirange' originated from a hybridization made in the late summer of 2005 in a controlled breeding program in Hillscheid, Germany. The female parent was the proprietary plant designated 'K03-8222-6', unpatented, with white, single-type flowers and distinctly zoned foliage.

The male parent of 'Fisblirange' was an unpatented hybrid seedling identified as 'k99-4355-5' with brilliant red, single-type flowers, and vigorous growth habit.

'Fisblirange' was selected as one flowering plant within the progeny of the stated cross in the spring of 2006 in a controlled environment in Galdar, Gran Canaria, Spain.

The first act of asexual reproduction of 'Fisblirange' was accomplished when vegetative cuttings were taken from the initial selection in the fall of 2006 in a controlled environment in Galdar, Gran Canaria, Spain.

Horticultural examination of plants grown from cuttings of the plant initiated in February of 2007 in Hillscheid, Germany, and continuing thereafter, has demonstrated that the combination of characteristics as herein disclosed for 'Fisblirange' are firmly fixed and are retained through successive generations of asexual reproduction.

'Fisblirange' has not been observed under all possible environmental conditions. The phenotype may vary significantly with variations in environment such as temperature, light intensity and day length.

Plant Breeder's Rights for this cultivar were applied for in Switzerland on Jun. 23, 2008 and in Canada on Mar. 9, 2009.

'Fisblirange' has not been made publicly available more than one year prior to the filing of this application.

BRIEF DESCRIPTION OF THE NEW VARIETY

The accompanying photographic drawings show typical flower and foliage characteristics of 'Fisblirange' with colors being as true as possible with an illustration of this type.

DETAILED BOTANICAL DESCRIPTION

Figure 1:
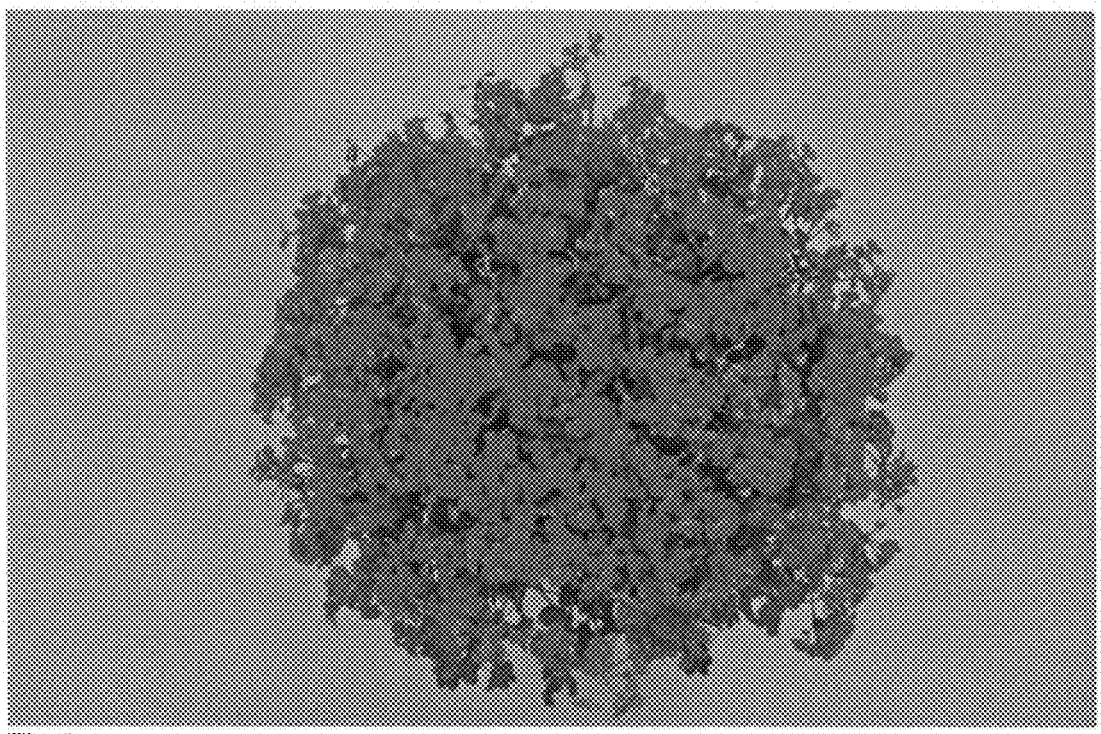
FIG. 1 shows a hanging basket in mid to late summer with three about 5-6 month old plants. The photograph was taken in Hillscheid, Germany in August 2008.
Figure 2:
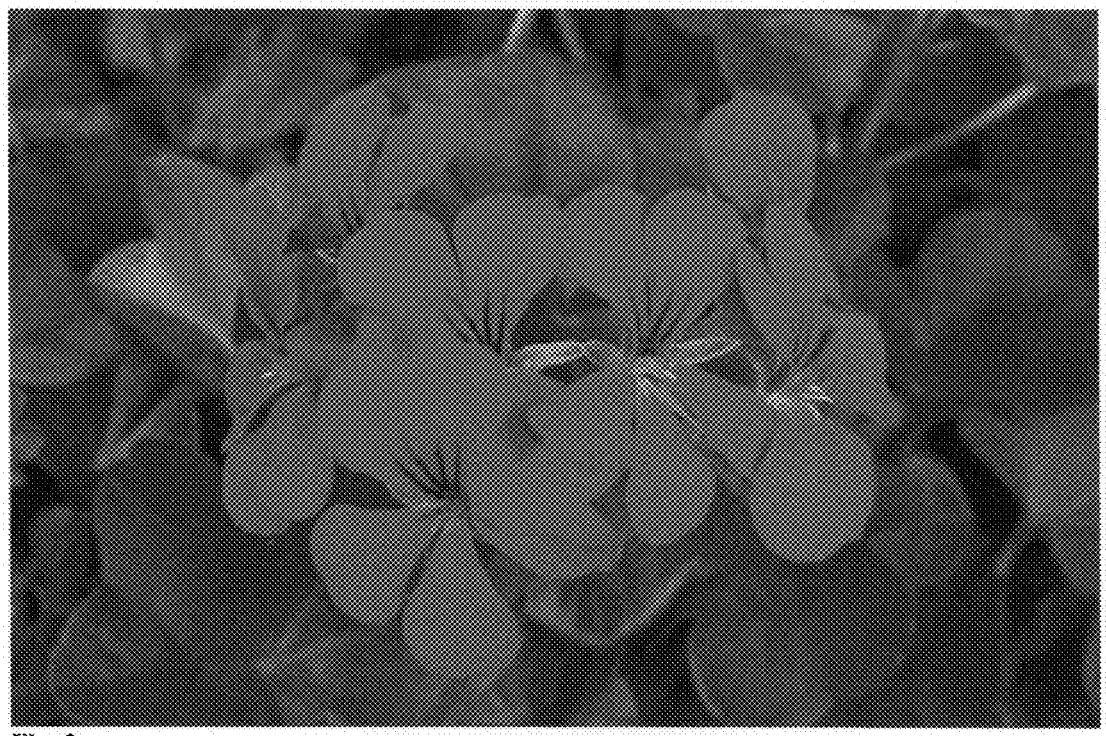
FIG. 2 is a close up view of the flowers.
Figure 3:
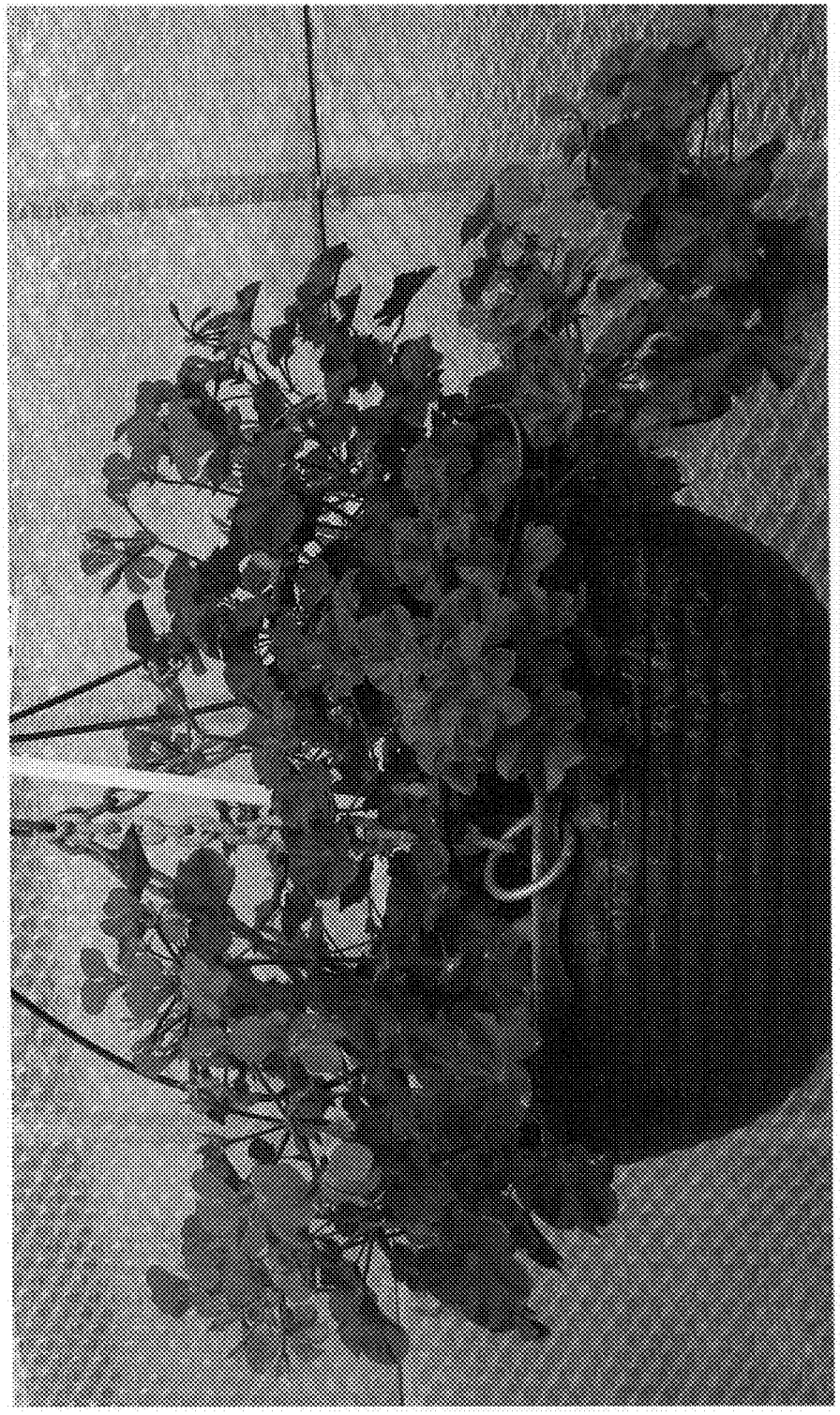
FIG. 3 shows a basket with younger, 15-16 week old plants, taken in Hillscheid, Germany in mid June 2008.

The measurements were taken in Hillscheid, Germany, on Apr. 29, 2009 on 12 week old plants that were growing in a greenhouse. Culture of these plants started in early February 2009, when rooted cuttings were planted into 12 cm pots, and were pinched once. Plant were grown out on benches at minimum day/night temperatures of (only) 14°/16° C. until April 1, and at higher temperatures thereafter.

Color Chart used: Royal Horticultural Society Colour Chart (R.H.S.) 2001

BRIEF SUMMARY OF INVENTION

The following observations, measurements, and comparisons describe plants grown indoors in Hillscheid, Germany and Chatellerault, France. The following traits have been repeatedly observed and are determined to be basic characteristics of the new variety. The combination of these characteristics distinguishes this new *Pelargonium* (common name: ivy geranium) as a new and distinct variety.

1. Bright red, single-type flowers
2. Large inflorescences on relatively long peduncles
3. Medium green, healthy foliage, no development of 'oedema'
4. Distinctly lobed leaves with weak to medium distinct zone 5. Vigorous growth, bushy, initially spreading, trailing plant habit
6. Freely branching
7. Early flowering and floriferous throughout the summer

DIFFERENCES BETWEEN THE NEW VARIETY 'FISBLIRANGE' AND SIMILAR VARIETIES

In comparison with 'Fisardred,' U.S. Plant patent application No. 12/221,492 (to be abandoned and replaced by the present application); 'Fisblirange' has slightly smaller and more rounded flowers, due to upper and lower petals of about the same size, while upper petals of 'Fisardred' are longer than the lower petals. Flower veins, pedicels and sepals develop less deep anthocyanin coloration, so they show less deep reddish or purple color. Furthermore, foliage of 'Fisblirange' has a much stronger leaf zone, and leaves have no tendency to developing leaf oedema in contrast to 'Fisardred.'

Plant:

*Form, growth and habit.*—Bushy, well-branching, initially spreading, then trailing, suitable especially for hanging baskets and window baskets.

*Plant height.*—17.3 cm.

*Plant height including inflorescene.*—Approximately 22-30 cm.

*Plant diameter.*—28.8 cm.

*Plant size at the end of the summer.*—80-90 cm (about 6 months old, measured from the base of the main stem to the tips of shoots).

Stem:

*Number of branches.*—8-13.

*Color of stem.*—RHS 143B-143C.

*Length of stem.*—14-20 cm.

*Diameter.*—4 mm.

*Length of internodes.*—2-4 cm.

*Texture.*—Very short pubescence.

Foliage:

*Immature leaf, color upper surface.*—RHS 137C to 137D.

*Immature leaf, lower surface.*—RHS 138A.

*Mature leaf, color upper surface.*—RHS 137B, medium-green.

*Mature leaf, color lower surface.*—Between RHS 137D to 143A.

*Length.*—7.6 cm.

*Width.*—4.0-4.7 cm.

*Shape.*—Ivy-shaped (palmatisect) with distinct lobes.

*Base shape.*—Cordate, open gap between lowest lobes.

*Apex shape.*—Rounded to acute.

*Margin.*—Mainly entire, weak crenation near the tips of lobes may occur.

*Texture.*—Leathery, surface appears smooth, dull to slightly glossy, upper surface glabrous, edge and underside covered with hair (hirtellous).

*Zone.*—Weak to medium distinctness, dark brown, RHS 166A.

*Color of veins, upper surface.*—Indistinct, RHS 137D.

*Color of veins, lower surface.*—RHS 143C.

*Petiole color.*—RHS 143A.

*Petiole length.*—Short, mostly from 2-6 cm.

*Diameter of petiole.*—2 mm.

*Texture.*—Pubescent.

Inflorescence:

*Begin of flowering.*—(50% of plants on Apr. 30, 2009 (12 week old) with open flowers).

*Duration of flowering.*—Continuous flowering throughout the Summer.

*Type.*—An umbel, irregular to nearly semi-spherical shape.

*Numbers of inflorescences per plant.*—8-11.

*Number of flowers per inflorescence.*—12.1 (11-15).

*Umbel diameter.*—10.4 cm.

*Umbel depth.*—5.5-6 cm.

*Durability of inflorescence on the plant.*—About 12-15 days, petals are self-cleaning (moderately 'shattering').

Peduncle:

*Color.*—RHS 143B to 143C, no anthocyanin.

*Length of peduncle.*—15.9 cm.

*Peduncle diameter.*—2.5 mm.

*Texture.*—Fine pubescence.

Pedicel:

*Color of pedicel.*—Purple, RHS 181A to 181B.

*Length of pedicel.*—3.4 cm.

*Diameter of pedicel.*—2 mm.

*Texture.*—Short pubescence, dense, no glandular hair.

Corolla:

*Form.*—Single-type, zygomorphic, open, with the petals mostly not overlapping, upper and lower petals of about same size.

*Diameter (length) of flower.*—4.9 cm.

*Depth of flowers.*—1.3-1.5 cm.

*Number of petals.*—5.

*Color upper petals, upper surface.*—Between RHS 45B and RHS 43A, at the base dark veins, RHS 187B or 187C.

*Color upper petals, lower surface.*—RHS 46C-46D.

*Length of upper petals.*—2.8-2.9 cm.

*Width of upper petals.*—1.6-1.7 cm.

*Color lower petals, upper surface.*—Near RHS 43A, no markings.

*Color lower petals, lower surface.*—RHS 46D.

*Length of lower petals.*—2.5-2.6 cm.

*Width of lower petals.*—1.6-1.8 cm.

*Petal shape.*—Spatulate (upper petals) and obovate (lower petals).

*Apex shape.*—Truncate or slightly retuse (upper petals); rounded (lower petals).

*Margin.*—Entire, possibly weakly crenulated at the apex.

*Petal texture.*—Smooth, glabrous.

*Number of petaloids.*—None.

Bud (just before opening):

*Color.*—Red, RHS 46C.

*Length.*—19-21 mm.

*Width.*—7-9 mm.

*Shape.*—Elliptic, narrow.

Calyx:

*Number of sepals.*—5.

*Color of sepals.*—Mainly green, RHS 143A, brownish 178A-178B for the largest sepal, visible (abaxial) side.

*Length of sepals.*—11-13 mm.

*Width of sepals.*—3-5 mm for the largest sepal, 3-4 mm for the other ones.

*Sepal shape.*—Lanceolate.

*Apex shape.*—Acute, pointed.

*Margins.*—Entire.

*Texture.*—Short hair, mostly at the base, a few longer, soft hairs.

Reproduction organs:

*Gynoecium.*—Pistil: One. Length: 11-12 mm. Style color: White to cream, RHS 155A to 158D. Style length: 5-6 mm. Stigma color: Deep red, RHS 53A to 53B.

*Androecium.*—Number of anthers: 7. Length of anthers: 2-3 mm. Anther color: RHS 187A, dark purple. Length filaments: 6-10 mm. Color of filaments: Mainly white, upper ends purple-pink, RHS N66D. Pollen amount: Typical. Color of pollen: Orange, RHS 25A.

Fertility:

*Seed set.*—No seed set observed.

Disease/pest resistance: Disease resistance or susceptibility has not been observed on this hybrid.

What is claimed is:

1. A new and distinct variety of *Pelargonium* plant named 'Fisblirange,' substantially as illustrated and described herein.

* * * * *